(12) United States Patent
Matoba et al.

(10) Patent No.: US 8,068,583 B2
(45) Date of Patent: Nov. 29, 2011

(54) X-RAY ANALYSIS APPARATUS AND X-RAY ANALYSIS METHOD

(75) Inventors: Yoshiki Matoba, Chiba (JP); Kanji Nagasawa, Chiba (JP)

(73) Assignee: SII Nanotechnology Inc. (JP)

( * ) Notice: Subject to any disclaimer, the term of this patent is extended or adjusted under 35 U.S.C. 154(b) by 143 days.

(21) Appl. No.: 12/494,851

(22) Filed: Jun. 30, 2009

(65) Prior Publication Data

US 2010/0002833 A1    Jan. 7, 2010

(30) Foreign Application Priority Data

Jul. 1, 2008   (JP) ................. 2008-172006
Oct. 29, 2008  (JP) ................. 2008-277731

(51) Int. Cl.
*G01B 15/00*   (2006.01)
*G01N 23/201*  (2006.01)

(52) U.S. Cl. .......................... 378/90; 378/88

(58) Field of Classification Search ............... 378/6, 46, 378/51, 53–58, 62, 70, 82–90, 98, 98.2, 98.8, 378/98.12, 210
See application file for complete search history.

(56) References Cited

U.S. PATENT DOCUMENTS

| | | | |
|---|---|---|---|
| 5,245,648 A * | 9/1993 | Kinney et al. ............ 378/43 |
| 6,765,205 B2 * | 7/2004 | Ochiai et al. ............ 850/9 |
| 7,289,598 B2 * | 10/2007 | Matoba ............ 378/46 |
| 7,583,789 B1 * | 9/2009 | MacDonald et al. ............ 378/84 |
| 2004/0234029 A1 * | 11/2004 | De Lange et al. ............ 378/70 |
| 2009/0196397 A1 * | 8/2009 | Bertozzi et al. ............ 378/87 |
| 2009/0262893 A1 * | 10/2009 | Stewart et al. ............ 378/62 |
| 2010/0034353 A1 * | 2/2010 | Kravis et al. ............ 378/87 |

FOREIGN PATENT DOCUMENTS

JP    04-175647    6/1992

* cited by examiner

*Primary Examiner* — Anastasia Midkiff
(74) *Attorney, Agent, or Firm* — Brinks Hofer Gilson & Lione

(57) ABSTRACT

Provided is an X-ray analysis apparatus including: an X-ray tubular bulb for irradiating a sample with a radiation beam; an X-ray detector for detecting a characteristic X-ray and a scattered X-ray and outputting a signal containing energy information on the characteristic X-ray and the scattered X-ray; an analyzer for analyzing the signal; a sample stage capable of moving an irradiation point relatively with respect to the sample within a mapping area set in advance; and an X-ray mapping processing section for discriminating an X-ray intensity corresponding to a specific element, determining an intensity contrast in which a color or lightness is changed in accordance with the X-ray intensity, and for performing image display at a position corresponding to the irradiation point, in which the X-ray mapping processing section determines the intensity contrast of the X-ray intensity at the irradiation point by setting in advance the X-ray intensity discriminated as to a reference material in which a component element and a concentration thereof are known as a reference.

10 Claims, 7 Drawing Sheets

X-RAY ANALYSIS APPARATUS AND X-RAY ANALYSIS METHOD

RELATED APPLICATIONS

This application claims priority under 35 U.S.C. §119 to Japanese Patent Application Nos. JP2008-172006 filed on Jul. 1, 2008 and JP2008-277731 filed on Oct. 29, 2008, the entire contents of which are hereby incorporated by reference.

BACKGROUND OF THE INVENTION

1. Field of the Invention

The present invention relates to an X-ray analysis apparatus and an X-ray analysis method which are suitable for performing an X-ray mapping analysis on a surface of a sample through, for example, a fluorescent X-ray analysis.

2. Description of the Related Art

A fluorescent X-ray analysis is used to perform a qualitative analysis or a quantitative analysis of a sample by radiating the sample with an X-ray emitted from an X-ray source, detecting a fluorescent X-ray which is a characteristic X-ray emitted from the sample with an X-ray detector, and by obtaining a spectrum from energy of the fluorescent X-ray. The Fluorescent X-ray analysis enables the non-destructive and quick analysis of the sample, and therefore the Fluorescent X-ray analysis is widely used in manufacturing process management, quality control, or the like. In recent years, precision and sensitivity have been increased in the X-ray analysis, which enables trace measurement. Accordingly, there is expected the diffusion of the X-ray analysis as an analysis technique of performing especially detection of a harmful substance contained in a material, a composite electronic component, or the like.

As analysis techniques in the Fluorescent X-ray analysis, there are a wavelength dispersive method for splitting a fluorescent X-ray by an analyzing crystal to measure a wavelength and an intensity of the X-ray, an energy dispersive method for detecting a fluorescent X-ray with a semiconductor detector without splitting the fluorescent X-ray to measure an energy and an intensity of the X-ray with a pulse height analyzer, and the like.

Conventionally, for example, JP04-175647A proposes an X-ray mapping device including an X-ray tube for irradiating a sample with an X-ray, an X-ray detector for detecting a fluorescent X-ray generated from the sample irradiated with the X-ray, a pulse processor for discriminating an element contained in the sample and its intensity based on an output of the X-ray detector, a computer to which a signal transmitted from the pulse processor is input, and an image processing system for processing an output of the computer to display a distribution of an X-ray intensity in a two-dimensional image.

However, the above-mentioned conventional technology has the following problem.

That is, the conventional device for performing X-ray mapping can discriminate a distribution of a specific element by colors or a contrast thereof on an image to some extent, based on a magnitude of the intensity of the X-ray. However, there is no reference of an element concentration, and hence it is difficult to recognize a distribution of an element which has a predetermined concentration or more directly from an image.

SUMMARY OF THE INVENTION

The present invention has been made in view of the above-mentioned problem, and therefore an object thereof is to provide an X-ray analysis apparatus and an X-ray analysis method capable of easily and directly recognizing and specifying a portion of a specific element, which has a predetermined concentration or more, from an image subjected to X-ray mapping.

In order to solve the above-mentioned problem, the present invention adopts the following structure. That is, an X-ray analysis apparatus according to the present invention includes: a radiation source for irradiating an irradiation point on a sample with a radiation beam; an X-ray detector for detecting a characteristic X-ray and a scattered X-ray which are radiated from the sample and outputting a signal containing energy information on the characteristic X-ray and the scattered X-ray; an analyzer for analyzing the signal; a moving mechanism capable of moving the irradiation point relatively with respect to the sample within a mapping area set in advance; and an X-ray mapping processing section for discriminating an X-ray intensity corresponding to a specific element from an analysis result obtained by the analyzer, determining an intensity contrast in which one of a color and lightness is changed in accordance with the X-ray intensity, and performing image display at a position corresponding to the irradiation point of the mapping area, in which the X-ray mapping processing section determines the intensity contrast of the X-ray intensity at the irradiation point by setting in advance, as a reference, the X-ray intensity discriminated as to a reference material in which a component element and one of a concentration and a thickness thereof are known.

Further, the present invention relates to an X-ray analysis method of irradiating an irradiation point on a sample with a radiation beam from a radiation source, detecting a characteristic X-ray and a scattered X-ray which are radiated from the sample by an X-ray detector, and outputting a signal containing energy information on the characteristic X-ray and the scattered X-ray, the X-ray analysis method including: analyzing the signal by an analyzer; moving, by a moving mechanism, the irradiation point relatively with respect to the sample within a mapping area set in advance; and performing image display at a position corresponding to the irradiation point of the mapping area by an X-ray mapping processing section by discriminating an X-ray intensity corresponding to a specific element from an analysis result obtained by the analyzer, and by determining an intensity contrast in which one of color and lightness is changed in accordance with the X-ray intensity, in which the performing image display includes determining, by the X-ray mapping processing section, the intensity contrast of the X-ray intensity at the irradiation point by setting in advance, as a reference, the X-ray intensity discriminated as to a reference material in which a component element and one of a concentration and a thickness thereof are known.

In the above-mentioned X-ray analysis apparatus and X-ray analysis method, the X-ray mapping processing section determines the intensity contrast of the X-ray intensity at the irradiation point by setting the X-ray intensity discriminated as to the reference material in which the component element and one of the concentration and the thickness thereof are known as the reference. Accordingly, it is possible to visually recognize whether the concentration of the specific component element is higher or lower or whether the thickness thereof is thicker or thinner compared with the reference with ease through a comparison between the X-ray intensity of the known reference material, which is set as the reference, and the X-ray intensity at the irradiation point of the sample and performing the mapping on a two-dimensional image.

Further, in the X-ray analysis apparatus according to the present invention: the reference material is located within the mapping area; and the X-ray mapping processing section discriminates the X-ray intensity of the reference material together with the sample and performs the image display.

Further, in the X-ray analysis method according to the present invention: the reference material is located within the mapping area; and the performing image display includes discriminating, by the X-ray mapping processing section, the X-ray intensity of the reference material together with the sample, and performing the image display.

That is, in the above-mentioned X-ray analysis apparatus and X-ray analysis method, the X-ray intensity is discriminated as to the reference material located within the mapping area together with the sample for the image display, and hence the reference material and the sample can be subjected to the X-ray mapping simultaneously, which results in labor saving in measuring the X-ray intensity of the reference material separately. Moreover, the analysis conditions (distance from the detector, atmosphere, and the like) in the case of discriminating the X-ray intensity are easily made to coincide with each other between the reference material and the sample, which suppresses variations due to an analysis environment.

Further, in the X-ray analysis apparatus according to the present invention, the reference material is placed on the sample. That is, the reference material is placed on the sample in the X-ray analysis apparatus, and thus a height of a component or a material located on the sample is substantially equal to a height of the reference material, which makes distances from the X-ray detector thereto equal to each other. Accordingly, detection accuracy with high X-ray intensity can be obtained.

Further, in the X-ray analysis apparatus according to the present invention, the X-ray mapping processing section sets an average value of the X-ray intensities of the reference material within a given area as the reference. In the case where the X-ray intensity obtained only at one point within the reference material is set as the reference, variations may occur in the reference due to the element distribution or the like of the reference material to some extent. In the X-ray analysis apparatus according to the present invention, however, the X-ray mapping processing section sets the average value of the X-ray intensities within the given area of the reference material as the reference. As a result, even when there are variations in element distribution to some extent, a highly accurate reference value with a few variations can be obtained by averaging the X-ray intensities.

Further, in the X-ray analysis apparatus according to the present invention, the X-ray mapping processing section sets the X-ray intensity of the reference material as one of an upper limit and a lower limit of the intensity contrast to perform the image display. That is, in the X-ray analysis apparatus, the X-ray mapping processing section performs the image display by setting the X-ray intensity of the reference material as the upper limit or the lower limit of the intensity contrast, whereby only the part in which an element concentration or a thickness exceeding the reference is detected is clearly displayed by the intensity contrast to be visible. Accordingly, the high-concentration part or the like can be easily specified more visibly. For example, in the case where the X-ray intensity of the reference material is set as the lower limit of the intensity contrast, the part having the X-ray intensity of the reference material serving as the reference or smaller, in which the element concentration or the thickness is detected, is displayed completely in black. Meanwhile, an image of the part having the X-ray intensity which is higher than that of the reference material is displayed with high visibility by the intensity contrast of a color other than black or high lightness.

Further, in the X-ray analysis apparatus according to the present invention, the X-ray mapping processing section is capable of superimposing an image of the X-ray intensity and one of an optical microscope image and a secondary electron image of the sample on each other to be displayed. That is, in the X-ray analysis apparatus, the X-ray mapping processing section is capable of superimposing the image of the X-ray intensity and the optical microscope image or the secondary electron image of the sample to be displayed, with the result that not only information on the X-ray intensity but also information obtained by the optical microscope image or the secondary electron image of the sample can be visually recognized simultaneously at each part. Accordingly, a malfunctioning part can be specified more easily.

Further, in the X-ray analysis apparatus according to the present invention: the sample is contained in a housing formed of a material through which the radiation beam can pass; and the X-ray mapping processing section sets the X-ray intensity of the reference material as a reference, the X-ray intensity being measured in a state in which the reference material is covered with a cover member that is formed of the same material and has the same thickness as the housing.

Further, in the X-ray analysis method according to the present invention: the sample is contained in a housing formed of a material through which the radiation beam can pass; and the performing image display includes setting the X-ray intensity of the reference material as a reference, the X-ray intensity being measured in a state in which the reference material is covered with a cover member that is formed of the same material and has the same thickness as the housing.

In the above-mentioned X-ray analysis apparatus and X-ray analysis method, the X-ray intensity of the reference material, which is measured in a state in which the reference material is covered with the cover member that is made of the same material and has the same thickness as the housing, is set as the reference, and thus a comparison is made between the X-ray intensity of the reference material, which is measured under the similar environment as the sample through the cover member that is formed of the same material and has the same thickness as the housing, and the X-ray intensity of the sample contained in the housing to be mapped on the secondary image. Accordingly, the sample covered with the housing can be analyzed without disintegrating the housing.

According to the present invention, the following effects can be achieved.

That is, according to the X-ray analysis apparatus and the X-ray analysis method of the present invention, the X-ray mapping processing section determines the intensity contrast of the X-ray intensity at the irradiation point by setting in advance the X-ray intensity discriminated as to the reference material in which the component element and the concentration or the thickness thereof are known as the reference, whereby it is possible to visually recognize with ease whether the specific element concentration is higher or lower or the thickness thereof is thicker or thinner compared with the reference material serving as the reference. Hence, it becomes possible to visually specify with ease, for example, the malfunctioning part which contains the specific element in higher concentration than prescribed.

DETAILED DESCRIPTION OF THE PREFERRED EMBODIMENTS

Hereinafter, an X-ray analysis apparatus and an X-ray analysis method according to an embodiment of the present invention is described with reference to FIGS. 1 to 5. In each of the drawings referred to in the following description, scale size is appropriately changed to illustrate each member in a recognizable manner.

Figure 1:
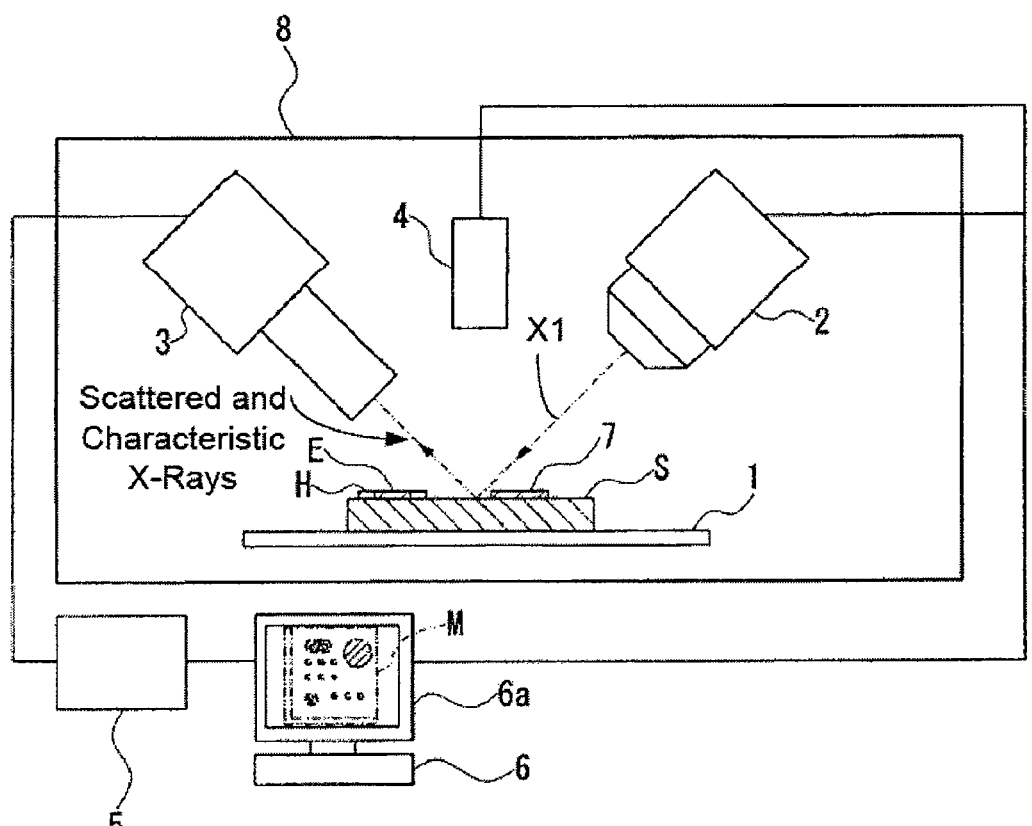
FIG. 1 is an entire configuration diagram schematically illustrating an X-ray analysis apparatus according to an embodiment of the present invention.
Figure 2:
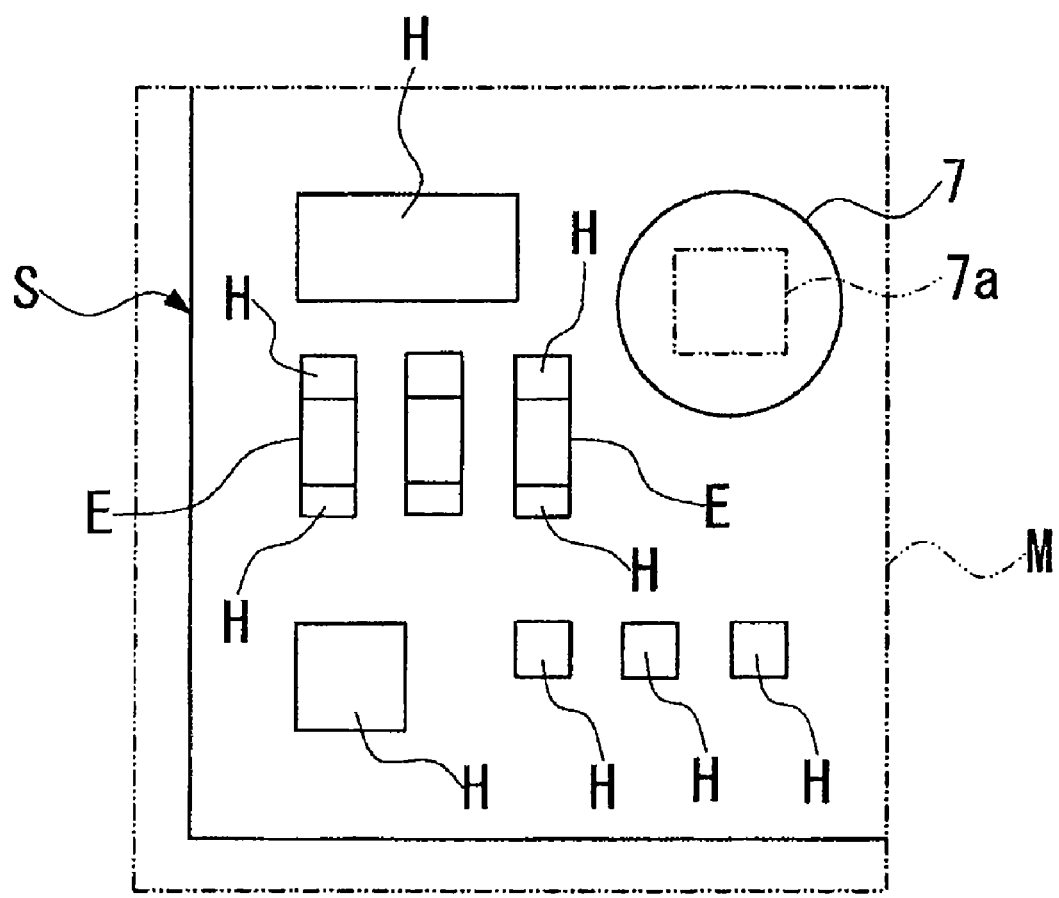
FIG. 2 is a plan view schematically illustrating a state in which a reference material is placed in a measurement area on a sample (electronic circuit board) in the embodiment.

The X-ray analysis apparatus according to this embodiment is, for example, an energy dispersive fluorescent X-ray analysis apparatus, and as illustrated in FIG. 1 and FIG. 2, includes: a movable sample stage (moving mechanism) 1 for placing a sample S thereon and moving the sample S; an X-ray tubular bulb (radiation source) 2 for irradiating a primary X-ray (radiation beam) X1 to an arbitrary irradiation point located on the sample S; an X-ray detector 3 for detecting a characteristic X-ray and a scattered X-ray which are radiated from the sample S and outputting a signal containing energy information on the characteristic X-ray and the scattered X-ray; an optical microscope 4 for acquiring an enlarged illumination image of the sample S, which is illuminated by an illumination unit (not shown), as an image date; an analyzer 5 connected to the X-ray detector 3 for analyzing the signal; and an X-ray mapping processing section 6 connected to the analyzer 5 for performing analysis processing so as to discriminate an X-ray intensity corresponding to a specific element and determining an intensity contrast in which a color or lightness is changed in accordance with the X-ray intensity thus obtained to perform image display at a position corresponding to the irradiation point on a display section 6a.

The X-ray tubular bulb 2 emits as the primary X-ray X1 an X-ray, which is generated by the fact that thermoelectrons generated from a filament (positive electrode) of the tubular bulb are accelerated by a voltage applied between the filament (positive electrode) and a target (negative electrode) to thereby impinge against the target of W (tungsten), Mo (molybdenum), Cr (chromium), or the like, from a window of a beryllium foil or the like.

The X-ray detector 3 includes a semiconductor detection element (for example, Si (silicon) element which is a pin-structure diode) (not shown) disposed to an incident window of the X-ray, and when one X-ray photon enters, a current pulse corresponding to the one X-ray photon is generated. A momentary current value of the current pulse is proportional to energy of the characteristic X-ray which enters. Further, the X-ray detector 3 is set so as to convert the current pulse generated in the semiconductor detection element into a voltage pulse, amplify the voltage pulse, and output the amplified voltage pulse as a signal.

The analyzer 5 described above is a pulse height analyzer (multi-channel pulse height analyzer) for obtaining a pulse height of the voltage pulse from the signal to generate an energy spectrum.

The X-ray mapping processing section 6 is a computer configured by a CPU and the like and functions as an analysis processing device, and has a function of discriminating the X-ray intensity corresponding to the specific element from an energy spectrum transmitted from the analyzer 5 and displaying a two-dimensional image subjected to the X-ray mapping based on the X-ray intensity on the display section 6a. In addition, the X-ray mapping processing section 6 is connected to the above-mentioned configuration and has a function of controlling the configuration, which is capable of displaying various items of information on the display section 6a in accordance with the control.

The X-ray mapping processing section 6 is set so that an average value of the X-ray intensities within a given area 7a of a reference material 7 becomes a reference. In addition, the X-ray mapping processing section 6 can be set so that image display is performed by setting the X-ray intensity of the reference material 7 as an upper limit or a lower limit of the intensity contrast. Further, the X-ray mapping processing section 6 can be set so that an image of the X-ray intensity is superimposed on the optical microscope image of the sample S to be displayed.

The sample stage 1, the X-ray tubular bulb 2, the X-ray detector 3, the optical microscope 4, and the like are accommodated in a sample chamber 8, and the sample chamber 8 is decompressed when measurement is performed so that the X-ray is not absorbed in an atmosphere in the air.

Further, the sample stage 1 is an XYZ stage which is capable of moving horizontally and vertically and adjusting a height thereof in a state in which the sample S is fixed by means of a stepping motor (not shown) or the like. The sample stage 1 is controlled by the X-ray mapping processing section 6 so that the irradiation point is caused to relatively move with respect to the sample S within a preset mapping area M.

Next, the X-ray analysis method using the X-ray analysis apparatus according to this embodiment is described with reference to FIG. 1 to FIG. 5. Note that an electronic circuit board in which various electronic components E such as a resistor are implemented by a solder material H, and a concentration distribution of lead (Pb) contained in the solder material H or the like is checked through the X-ray mapping.

First, the sample S is set on the sample stage 1 and the mapping area M to be subjected to the X-ray mapping is input to the X-ray mapping processing section 6 to be set. Further, as illustrated in FIG. 2, the reference material 7 is placed on a space which is located within the mapping area M on the sample S and does not affect the measurement.

The sample chamber 8 is decompressed to be a predetermined pressure in this state. The reference material 7 is a material which has a known component element and concentration, such as a material which contains any element of lead, cadmium, chrominum, and the like and has a known concentration. Note that in this embodiment, in order to check the concentration distribution of lead (Pb) through the X-ray mapping, the reference material 7 which is formed of a solder material having Pb of 1,000 ppm in a disk shape is mounted on the sample S which is the electronic circuit board. Further, a height of the reference material 7 is set to be a height of the electronic component E or the solder material H on the sample S, which is to be analyzed.

Next, the sample stage 1 is driven to move the sample S directly below the optical microscope 4, and the mapping area M of the sample S is shot by the optical microscope 4 in a state in which the reference material 7 is placed on the sample S, whereby an optical microscope image thereof is transmitted to the X-ray mapping processing section 6 to be stored. Note that the mapping area M is set in advance and then shot by the optical microscope 4 through the above-mentioned procedure. However, a vicinity on an area of the sample S, which is expected to be analyzed, may be shot by the optical microscope 4, and the mapping area M may be set on the basis of an optical microscope image thereof. Also in this case, the setting is made such that the reference material 7 is included in the mapping area M.

Next, in order to perform fluorescent X-ray analysis, the X-ray mapping processing section 6 drives the sample stage 1 to move the sample S, and places an initial irradiation point within the mapping area M at an irradiation point of a primary X-ray X1 emitted from the X-ray tubular bulb 2. The sample S is irradiated with the primary X-ray X1 from the X-ray tubular bulb 2 in this state, whereby a characteristic X-ray and a scattered X-ray thus generated are detected by the X-ray detector 3.

The X-ray detector 3 detects the X-ray and then transmits a signal thereof to the analyzer 5, and the analyzer 5 extracts an energy spectrum from the signal and outputs the extracted spectrum to the X-ray mapping processing section 6. The X-ray mapping processing section 6 discriminates an X-ray intensity corresponding to a specific element (in this embodiment, lead) from the energy spectrum transmitted from the analyzer 5, and stores the X-ray intensity together with coordinate information on the irradiation point.

Further, the irradiation point is caused to be sequentially moved at predetermined distance intervals in the mapping area M, and is scanned in matrix, that is, scanned two-dimensionally. Then, the detection as described above is repeated for a plurality of irradiation points over the entire mapping area M, whereby the coordinate information on the respective irradiation points and the X-ray intensity of the specific element are stored. Specifically, the X-ray intensity of the reference material 7 is discriminated and stored together with that of the sample S within the mapping area M.

Figure 3:
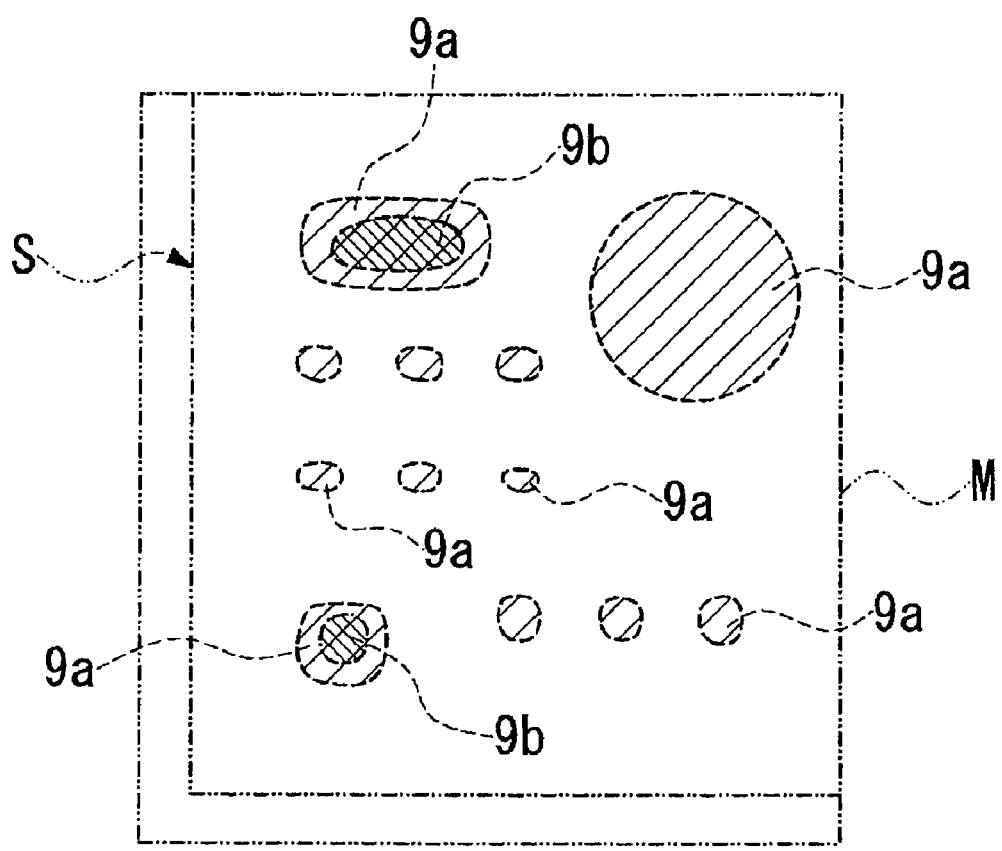
FIG. 3 is a schematic view illustrating image display of an X-ray intensity in a case where the measurement area on the sample (electronic circuit board) is subjected to X-ray mapping in the embodiment.

Next, the X-ray mapping processing section 6 determines an intensity contrast in which a color or lightness is changed in accordance with the X-ray intensity obtained in the above-mentioned detection by setting one irradiation point as one pixel, and as illustrated in FIG. 3, displays the intensity contrast two-dimensionally as an image at a position corresponding to the irradiation point of the display section 6a. In this case, the X-ray mapping processing section 6 determines the intensity contrast of the X-ray intensity at each irradiation point with the X-ray intensity detected from the reference material 7 on the sample S as a reference. In addition, as illustrated in FIG. 2, the X-ray mapping processing section 6 sets the intensity contrast with an average value of the X-ray intensities obtained at the plurality of irradiation points of a given area 7a of the reference material 7 as the reference. Note that in the case of setting the given area 7a, a boundary of the given area 7a is determined in, for example, a circular or quadrangular shape, which is input to the X-ray mapping processing section 6.

For example, as illustrated in FIG. 3, image display is performed by an intensity contrast 9a of the same lightness and color as those of the X-ray intensity of the reference material 7 at the irradiation point at which the X-ray intensity which is equal to or smaller than the X-ray intensity of the reference material 7 is detected for lead. Meanwhile, image display is performed by an intensity contrast 9b of other color or lightness which is higher than that of the X-ray intensity of the reference material 7, which serves as the reference, at the irradiation point at which the X-ray intensity which is higher than the X-ray intensity of the reference material 7 is detected.

In other words, lead contained in the reference material 7 is 1,000 ppm in this embodiment, and hence an image of a part on the sample S, in which the lead concentration is low to be equal to or smaller than 1,000 ppm, is displayed by the same intensity contrast 9a as that of the reference material 7. Meanwhile, an image of a part on the sample S, in which the lead concentration is high to exceed 1,000 ppm, is displayed by the intensity contrast 9b of other color or lightness which is higher than that of the reference material 7. In this manner, image display is performed with a visually apparent difference therebetween.

Figure 4:
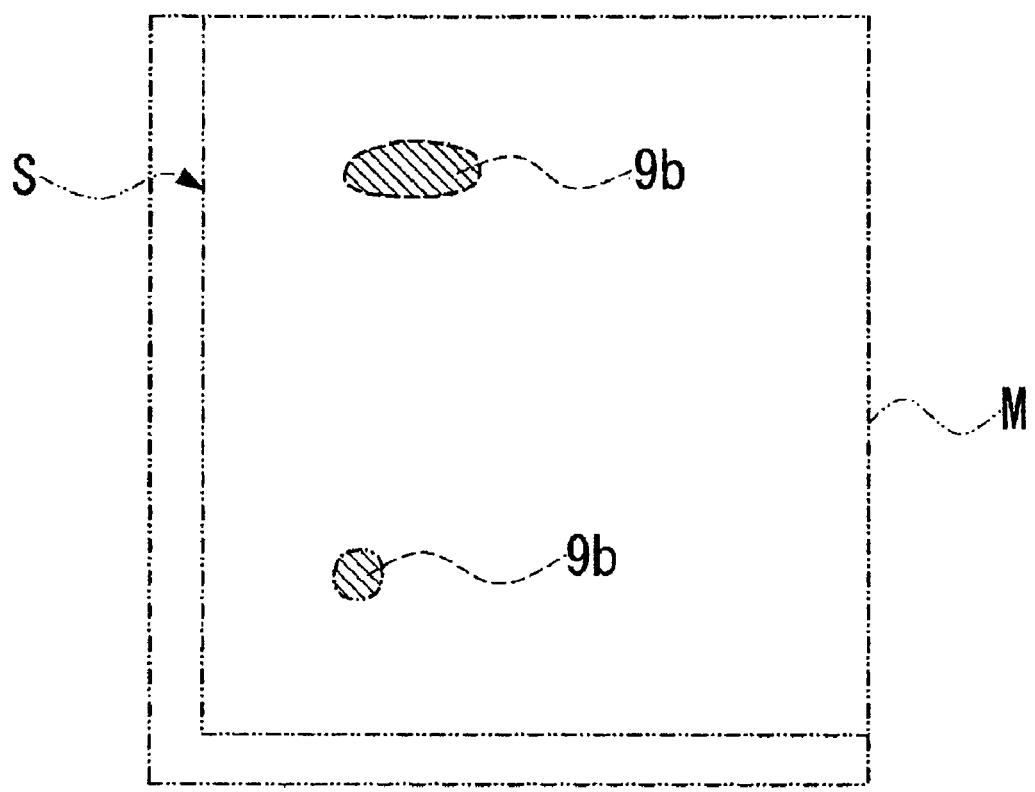
FIG. 4 is another schematic view illustrating the image display of the X-ray intensity by setting an X-ray intensity of the reference material as a lower limit of an intensity contrast in the case where the measurement area on the sample (electronic circuit board) is subjected to the X-ray mapping in the embodiment.

Next, in order to clearly display only the part which contains lead of concentration more than that of the reference material 7, setting of image processing performed by the X-ray mapping processing section 6 is changed, and the X-ray intensity of the reference material 7 is set to the upper limit or the lower limit of the intensity contrast for image display. For example, as illustrated in FIG. 4, in the case where the X-ray intensity of the reference material 7 is set as the lower limit of the intensity contrast, the part in which the X-ray intensity which is equal to or smaller than the X-ray intensity of the reference material 7 serving as the reference is displayed completely in black (in FIG. 4, a black portion is not shown but displayed in white for easy understanding), while the part in which the X-ray intensity is larger than that of the reference material 7 is displayed with high viewability by the intensity contrast 9b of a color other than black (for example, red) or high lightness. Specifically, only a high-concentration part of more than 1,000 ppm is prominently displayed with high viewability, and hence the high-concentration part can be specified at a glance.

Note that in the case where the X-ray intensity of the reference material 7 is set as the upper limit of the intensity contrast, for example, the part in which the X-ray intensity which is equal to or smaller than the X-ray intensity of the reference material 7 serving as the reference may be displayed completely in white, while the part in which the X-ray intensity is larger than that of the reference material 7 may be displayed with high viewability by the intensity contrast (for example, black) of a color other than white and low lightness.

Figure 5:
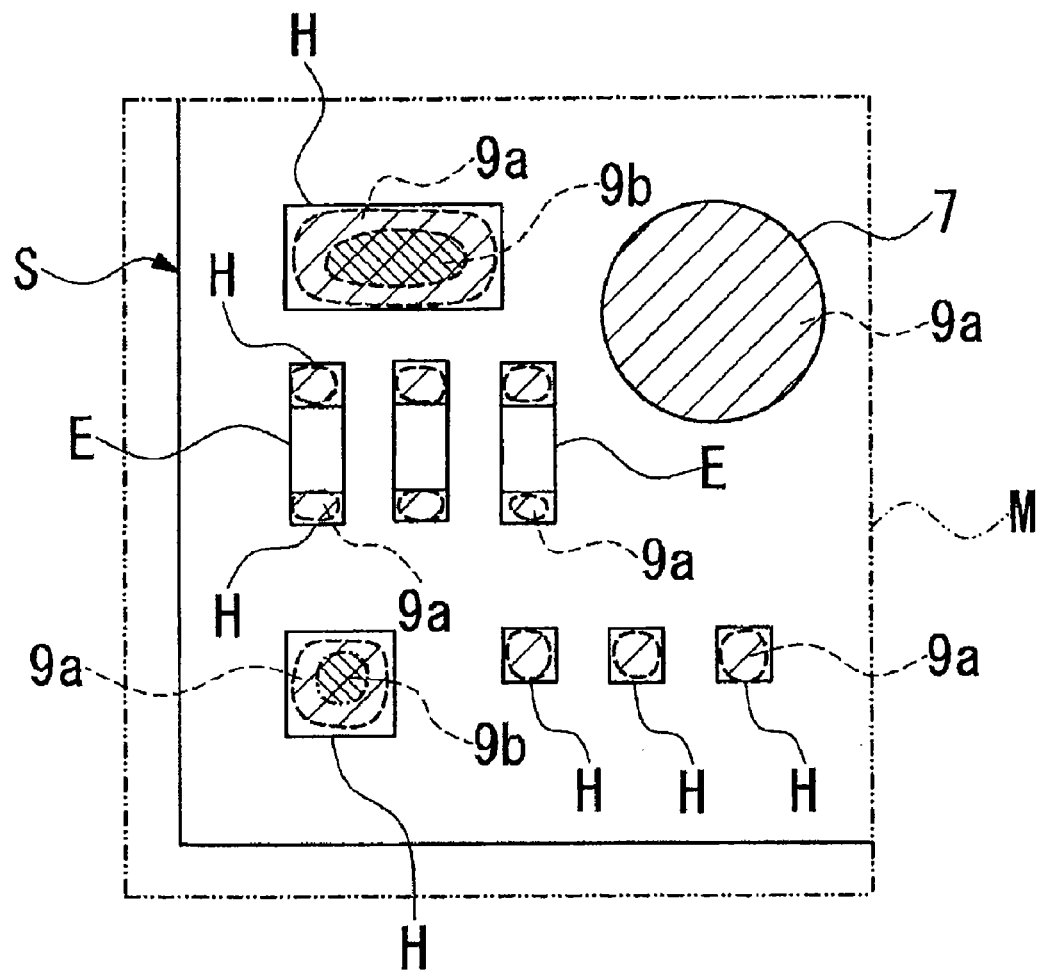
FIG. 5 is a schematic view illustrating image display in which an image of the X-ray intensity and an optical microscope image are superimposed on each other in the case where the measurement area on the sample (electronic circuit board) is subjected to the X-ray mapping in the embodiment.

Next, the setting of the image processing performed by the X-ray mapping processing section 6 is changed for grasping a positional relationship between the distribution of the X-ray intensity (concentration distribution of lead) and an actual solder material H or electronic component E located on the sample S, and as illustrated in FIG. 5, the optical microscope image shot by the optical microscope 4 is superimposed on the image of the X-ray intensity, which is subjected to the X-ray mapping, to be displayed on the display section 6a. Accordingly, it becomes possible to easily grasp, on the same screen, a relationship between the concentration distribution of lead and the solder material H or the electronic component E located on the electronic circuit board, which is obtained through the X-ray mapping.

As described above, in the X-ray analysis apparatus according to this embodiment, the X-ray mapping processing section 6 determines the intensity contrast at the irradiation point with the X-ray intensity which is discriminated in advance as to the reference material 7 having the known component element and concentration as the reference. Accordingly, the X-ray intensity of the reference material 7 known as the reference and the X-ray intensity at the irradiation point of the sample S are compared with each other to be mapped on a two-dimensionally image, whereby it is possible to visually recognize with ease whether or not a concentration of a specific element is higher or lower than the reference.

Further, image display is performed for the reference material 7 located in the mapping area M by discriminating its X-ray intensity together with the sample S, and thus the reference material 7 and the sample S can be subjected to the X-ray mapping at the same time, which saves the inconvenience of measuring the X-ray intensity of the reference material 7 separately. Moreover, analysis conditions (distance from the X-ray detector 3, atmosphere, or the like) in the case of discriminating the X-ray intensity can be easily made to coincide with each other between the reference material 7 and the sample S, with the result that variations due to an analysis environment can be suppressed. In particular, the reference material 7 is placed on the sample S, and hence heights of the electronic component E and the solder material H located on the sample S and a height of the reference material 7 become equal to each other, which makes distances from the X-ray detector 3 thereto equal to each other. Accordingly, detection accuracy with high X-ray intensity can be obtained.

Further, the X-ray mapping processing section 6 sets the average value of the X-ray intensities within the given area 7a of the reference material 7 as the reference, and hence a reference value with high accuracy and few variations can be obtained by averaging the X-ray intensities even when there exist variations in element distribution to some extent.

Note that the X-ray intensity is detected for X-ray mapping in the state in which the reference material 7 is placed on the sample S, whereby the height of the solder material H or the like located on the sample S to be analyzed and the height of the reference material 7 become substantially equal to each other. Accordingly, detection accuracy with high X-ray intensity can be obtained.

Further, the X-ray mapping processing section 6 sets the X-ray intensity of the reference material 7 as the upper limit or the lower limit of the intensity contrast for image display, with the result that high-concentration part can be more visually specified with ease by clearly displaying only the part in which the element concentration exceeding the reference is detected by high contrast to be visible.

Moreover, the X-ray mapping processing section 6 is capable of superimposing the image of the X-ray intensity on the optical microscope image of the sample S to be displayed, whereby not only information on the X-ray intensity (that is, element concentration) but also arrangement information on the solder material H, the electronic component E, or the like, which can be obtained by the optical microscope image of the sample S, can be visually recognized simultaneously at each part. Accordingly, a malfunctioning part can be specified more easily.

Next, a method of analyzing a sample contained in a housing with the use of the X-ray analysis apparatus according to this embodiment is described with reference to FIG. 6 and FIGS. 7A and 7B.

Figure 6:
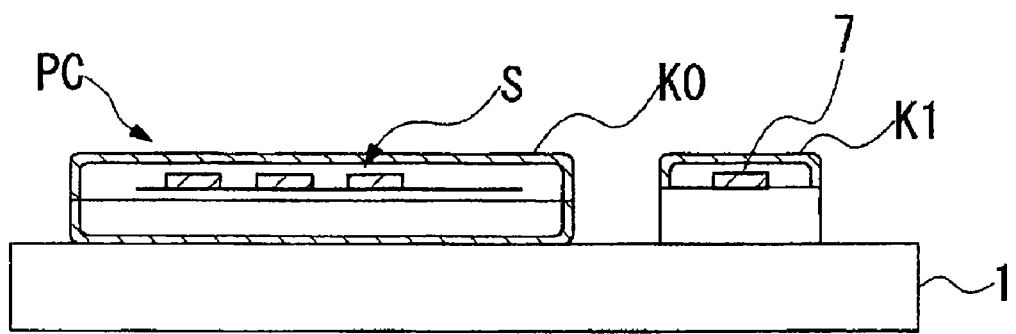
FIG. 6 is a cross-sectional view of a sample stage, illustrating a state in which the sample and the reference material are located when the sample contained in a housing is analyzed in the embodiment.
Figure 7A:
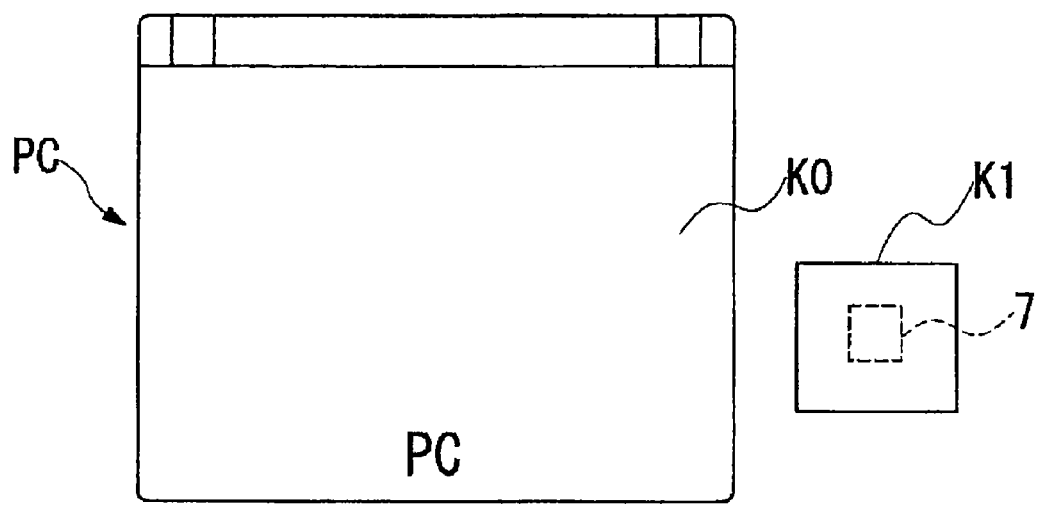
FIGS. 7A and 7B are views each schematically illustrating, as an example when the sample contained in the housing is analyzed, a camera image of a laptop computer and an analysis image of an inside thereof in the embodiment.

In this analysis method, as illustrated in FIG. 6 and FIG. 7A, analysis is performed with the circuit board or the like, which is contained in a housing K0 of a laptop computer as, for example, an electronic device, as the sample S.

When this analysis is performed, the reference material 7 is placed on the sample stage 1 together with the laptop computer PC. In this case, the reference material 7 is located in the state of being covered with a cover member K1 that is made of the same material and has the same thickness as the housing K0.

Figure 7B:
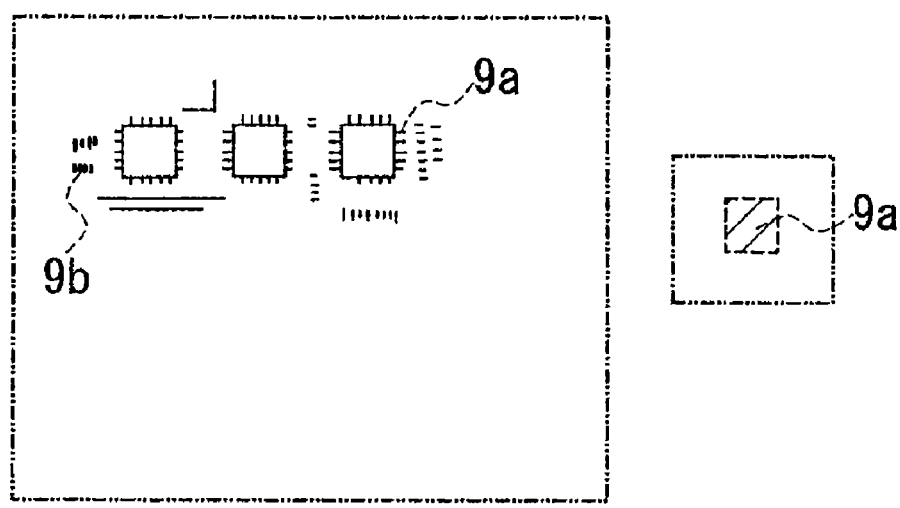

In this state, as illustrated in FIG. 7B, the X-ray mapping processing section 6 determines the intensity contrast of the X-ray intensity at the irradiation point as to the reference material 7 in the state of being covered with the cover member K1 with the X-ray intensity discriminated through the cover member K1 as the reference.

Conventionally, the electronic device such as the laptop computer PC is covered with the housing K0 formed of a covering material such as plastic or thin aluminum, and thus the X-ray from an object element is absorbed by housing K0 even when element analysis is performed on the sample S such as the circuit board contained in the housing K0 while being covered therewith, which extremely reduces its intensity. For this reason, a reduction in X-ray intensity, which is due to absorption, is large even when the X-ray intensity mapping is performed from the sample S, which makes it difficult to grasp the element concentration of the sample S.

However, in this embodiment, in the mapping analysis of the sample S contained in the housing K0 formed of a material through which the primary X-ray is capable of passing, the X-ray mapping processing section 6 sets the X-ray intensity of the reference material 7, which is measured in a state in which the reference material 7 is covered with the cover member K1 that is made of the same material and has the same thickness as the housing K0, as the reference in the case of image display. Accordingly, the X-ray intensity of the reference material 7, which is measured under the similar environment to that for the sample S through the cover member K1, and the X-ray intensity of the sample S contained in the housing K0 are compared with each other to be mapped on a two-dimensionally image, with the result that the sample S being covered with the housing K0 can be analyzed without being disintegrated.

In other words, the X-ray intensity of the reference material 7, which is measured through the cover member K1, is set as the reference, and hence X-ray absorption by the housing K0 can be taken into consideration. Therefore, the element analysis of the sample S such as the circuit board contained in the housing K0 can be performed while the sample S is covered with the housing K0. For example, according to this analysis method, as illustrated in FIG. 7B, an analysis image of lead (Pb) or the like of the sample S contained in the laptop computer PC can be displayed with respect to a camera image of the laptop computer PC illustrated in FIG. 7A.

In this case, as to lead, an image of the irradiation point inside the housing K0 through the cover member K1, at which the X-ray intensity which is equal to or smaller than the X-ray intensity of the reference material 7 is detected, is displayed by the intensity contrast 9a of the same lightness and color as those of the X-ray intensity of the reference material 7. In addition, an image of the irradiation point inside the housing K0 through the cover member K1, at which the X-ray intensity higher than the X-ray intensity of the reference material 7 is detected, is displayed by the intensity contrast 9b of a different color or lightness higher compared with the X-ray intensity of the reference material 7, which serves as the reference.

In this manner, in the case of checking presence or absence of a harmful element contained in the electronic device, screening can be performed without disintegrating the component containing the harmful element in the electronic device, which results in great labor saving in checking.

Note that a shape or the like of the substrate contained in the electronic device can be obtained as an analysis image when the object element to be detected is replaced by an element which has high X-ray energy.

Note that the technical scope of the present invention is not limited to the embodiment described above, and various changes can be made without departing from the gist of the present invention.

For example, the description has been made on the energy dispersive fluorescent X-ray analysis apparatus in the embodiment described above, but the present invention is applicable to other analysis system such as a wavelength dispersive fluorescent X-ray analysis apparatus or a scanning electron microscope-energy dispersive X-ray spectrometer (SEM-EDS) in which an electron beam is used as a radiation beam to be irradiated and a secondary electron image can be obtained as well.

Further, the description has been made in the embodiment described above that the X-ray mapping processing section 6 can superimpose the image of the X-ray intensity and the optical microscope image of the sample S on each other to be displayed. However, the image of the X-ray intensity and the secondary electron image may be superimposed on each other to be displayed in the case where the present invention is adopted in the SEM-EDS.

Further, one reference material which has known element concentration is used in the embodiment described above. However, another reference material which has different element concentration may be placed simultaneously on the sample, and the X-ray intensities may be detected with those two reference materials as the references for performing the X-ray mapping. In this case, the X-ray intensities of the two reference materials are each set as the upper limit and the lower limit of the intensity contrast, with the result that an image of the element distribution limited to a specific concentration range can be displayed. For example, a concentration range of an element such as Sn, Ag, or Cu is specified, and an image of a distribution thereof can be displayed with ease.

Further, the analysis is performed by making the sample chamber to be in a decompressed atmosphere in the embodiment described above, but may be performed in a state other than a vacuum (decompressed) atmosphere.

Moreover, the X-ray mapping is preferably performed by placing the reference material on the sample as described above, but the X-ray mapping may be performed by placing the reference material beside the sample within the mapping area M.

Further, the X-ray mapping is performed on the element concentration of the sample with the use of a reference material which has the known concentration of the component element in the embodiment described above. However, the X-ray mapping may be performed on the thickness of the sample with the use of the reference material which has the known thickness of the component element by the similar technique as described above with the X-ray intensity of the reference material as the reference.

What is claimed is:

1. An X-ray analysis apparatus, comprising:
   a radiation source for irradiating an irradiation point on a sample with a radiation beam;
   an X-ray detector for detecting a characteristic X-ray and a scattered X-ray which are radiated from the sample and outputting a signal containing energy information on the characteristic X-ray and the scattered X-ray;
   an analyzer for analyzing the signal;
   a moving mechanism capable of moving the irradiation point relatively with respect to the sample within a mapping area set in advance; and
   an X-ray mapping processing section for discriminating an X-ray intensity corresponding to a specific element arranged on the sample from an analysis result obtained by the analyzer, determining an intensity contrast in which one of a color and lightness is changed in accordance with the X-ray intensity, and performing image display at a position corresponding to the irradiation point of the mapping area,
   wherein the X-ray mapping processing section sets in advance, as a reference, the X-ray intensity discriminated as to a reference material arranged on the sample on which the specific element is arranged and a component element and one of a concentration and a thickness of the reference material being known, and the X-ray mapping processing section determines the intensity contrast of the X-ray intensity of the specific element discriminated as to the reference at the irradiation point;
   wherein a height of the reference material is set to be a height of the specific element arranged on the sample such that the X-ray mapping processing section determines the intensity contrast of the X-ray intensity when a distance from the X-ray detector to the reference material is equal to a distance from the X-ray detector to the specific element.

2. An X-ray analysis apparatus according to claim 1, wherein:
   the reference material is located within the mapping area; and
   the X-ray mapping processing section discriminates the X-ray intensity of the reference material together with the sample and performs the image display.

3. An X-ray analysis apparatus according to claim 2, wherein the reference material is placed on the sample.

4. An X-ray analysis apparatus according to claim 1, wherein the X-ray mapping processing section sets an average value of the X-ray intensities of the reference material within a given area as the reference.

5. An X-ray analysis apparatus according to claim 1, wherein the Xray mapping processing section sets the X-ray intensity of the reference material as one of an upper limit and a lower limit of the intensity contrast to perform the image display.

6. An X-ray analysis apparatus according to claim 1, wherein the X-ray mapping processing section is capable of superimposing an image of the X-ray intensity and one of an optical microscope image and a secondary electron image of the sample on each other to be displayed.

7. An X-ray analysis apparatus according to claim 1, wherein:
   the sample is contained in a housing formed of a material through which the radiation beam can pass; and
   the X-ray mapping processing section sets the X-ray intensity of the reference material as a reference, the X-ray intensity being measured in a state in which the reference material is covered with a cover member that is formed of the same material and has the same thickness as the housing.

8. An X-ray analysis method of irradiating an irradiation point on a sample with a radiation beam from a radiation source,
arranging a specific element and a reference material on the sample where a component element and one of a concentration and a thickness of the reference material are known, further comprising;
setting a height of the reference material to be a height of the specific element arranged on the sample;
detecting, with an X-ray detector, a characteristic X-ray and a scattered X-ray which are radiated from the sample;
detecting, with the X-ray detector, the characteristic X-ray and the scattered X-ray which are radiated from the reference material;
wherein a detection distance from the X-ray detector to the reference material is equal to the detection distance from the X-ray detector to the specific element;
outputting a signal containing energy information on the characteristic X-ray and the scattered X-ray;
analyzing the signal with an analyzer;
moving, with a moving mechanism, the irradiation point relatively with respect to the sample within a mapping area set in advance; and
performing image display at a position corresponding to the irradiation point of the mapping area with an X-ray mapping processing section by discriminating an X-ray intensity corresponding to a specific element arranged on the sample from an analysis result of the X-ray intensity of the reference material obtained by the analyzer, and by determining an intensity contrast in which one of color and lightness is changed in accordance with the X-ray intensity,
wherein the performing image display includes setting in advance, as a reference, the X-ray intensity discriminated as to the reference material and determining, with the X-ray mapping processing section, the intensity contrast of the X-ray intensity of the specific element discriminated as to the reference at the irradiation point.

9. An X-ray analysis method according to claim 8, wherein:
the reference material is located within the mapping area; and
the performing image display includes discriminating, with the X-ray mapping processing section, the X-ray intensity of the reference material together with the sample, and performing the image display.

10. An X-ray analysis method according to claim 8, wherein:
the sample is contained in a housing formed of a material through which the radiation beam can pass; and
the performing image display includes setting the X-ray intensity of the reference material as a reference, the X-ray intensity being measured in a state in which the reference material is covered with a cover member that is formed of the same material and has the same thickness as the housing.

* * * * *